United States Patent [19]

D'Silva

[11] Patent Number: 5,557,098
[45] Date of Patent: Sep. 17, 1996

[54] SYSTEM TO IDENTIFY BAGS DISINFECTED BY IRRADIATION WHICH PUNCHES HOLES IN A POLARIZED PORTION OF THE BAG TO INDICATE PROCESSING THEREOF

[75] Inventor: Edmund D. D'Silva, Vernon Hills, Ill.

[73] Assignee: Baxter International Inc., Deerfield, Ill.

[21] Appl. No.: 359,662

[22] Filed: Dec. 20, 1994

[51] Int. Cl.⁶ .................................................. H01J 40/14
[52] U.S. Cl. ................................. 250/222.1; 250/559.4; 250/223 B; 340/686; 356/39; 356/240
[58] Field of Search ................... 250/222.1, 559.4, 250/223 B, 225; 340/686, 679, 674; 356/39, 240

[56] References Cited

U.S. PATENT DOCUMENTS

| | | | |
|---|---|---|---|
| 3,316,411 | 6/1963 | Linderman | 250/559.4 |
| 3,677,627 | 2/1971 | Johnston et al. | 250/559.4 |
| 3,838,291 | 9/1974 | Marion et al. | 250/559.4 |
| 4,205,769 | 6/1980 | Blitchington | 250/559.4 |
| 4,866,282 | 9/1989 | Miripol et al. | |
| 4,952,812 | 8/1990 | Miripol et al. | |
| 5,141,110 | 8/1992 | Trischan et al. | 250/223 B |
| 5,290,221 | 3/1994 | Wolf, Jr. et al. | |
| 5,296,715 | 3/1994 | Kronberg | 250/551 |
| 5,305,081 | 4/1994 | Gooch et al. | 250/223 B |

Primary Examiner—Stephone Allen
Attorney, Agent, or Firm—Robert M. Barrett; Bradford R. L. Price; Joseph B. Barrett

[57] ABSTRACT

A system and a method are provided for detecting a bag that has been subjected to a process, such as illumination, wherein the contents of the bag require processing before subsequent use. The system (1) has a drawer (10) on which one or more bags may be placed and properly oriented. Punches (22) are provided for punching slugs from the bag indicative of a status of the processing of the bag. The punches (22) are aligned with die apertures (26) of a die (24) and corresponding punch apertures (20) through the drawer (10). The bag may include polarizing materials (50) such that the status of the processing of the bag (52) may be sensed. To this end, a rotating polarizing piece (70) is provided as well as a light source (34) and a sensor (38). The polarities between the polarizing piece (50) of the bag and the rotating polarizing piece (70) is monitored by the sensor (38) to indicate a condition or status of the processing of the bag and/or to further indicate tampering taking place in the process.

23 Claims, 5 Drawing Sheets

SYSTEM TO IDENTIFY BAGS DISINFECTED BY IRRADIATION WHICH PUNCHES HOLES IN A POLARIZED PORTION OF THE BAG TO INDICATE PROCESSING THEREOF

BACKGROUND OF THE INVENTION

The present invention generally relates to a system and a method to mark and/or identify a bag or container for holding a fluid therein. More specifically, the present invention relates to a system and a method for marking and/or identifying a disposable plastic bag or container having an interior for holding a mixture of methylene blue and a blood component, such as plasma. The system marks the bag to indicate whether the bag has been subjected to a process, such as an illumination process, used to treat the mixture, such as for sterilization.

It is, of course, generally known to provide containers having an interior for holding a variety of solutions, fluids, mixtures and the like. Such known bags and containers include a blood product, such as plasma. Viral inactivation is required following introduction of the blood product into the bag. To this end, the bag contains a chemical, such as methylene blue, which is mixed with the blood product. The mixture within the bag is then subjected to intense light of a prescribed wavelength, such as ultraviolet (UV), to photo-activate the chemicals in the bag which, in turn, perform the virucidal action on the blood product.

The photochemical reaction between the intense light and the product within the bag, however, does not produce any easily distinguishable sign indicating that the bag and the product therein has been subjected to a particular treatment. It is important to know whether such a bag and its contents, however, have been subjected to the illumination process. Visual inspection of the contents of the bag is virtually impossible following many treatment processes, particularly where distinguishing between a bag that has been illuminated and one that has not been illuminated is required.

Other systems are known to alleviate this problem and provide positive indication of the bag subjected to illumination. Such systems include application of a bar code identification to bags following subjection to the illumination, application of labels to illuminated bags, paint-marking the bag and/or use of a hot stamp to identify the bag. All of these known systems depend on cooperation and vigilance on the part of the user and can be easily defeated by the users or other individuals involved in the process. Furthermore, some of the systems, such as the bar code identification system, require additional individual illumination machines capable of communicating with a central computer to ensure that data was properly entered into a central data base.

A need, therefore, exists to provide a system and a method for marking and/or identifying a bag which provides positive identification that the bag has been subjected to a process, such as illumination, wherein the process is difficult to detect following completion of the process.

SUMMARY OF THE INVENTION

The present invention provides a system and a method for detecting status of a container holding a product wherein the product must be subjected to a process.

To this end, in an embodiment, a system for detecting status of a container having an interior holding a product requiring the product to be subjected to a process is provided. The system has a tray on which a container is placed. A light source is positioned to transmit a beam of light through the container. A sensor is constructed and arranged to detect the beam of light and its intensity.

In an embodiment, a rotating polarizer is constructed and arranged to rotate in the beam of light.

In an embodiment, a static polarizer is attached to the container wherein the static polarizer is capable of having a punch made therethrough.

In an embodiment, a plurality of receiving sections in the tray is capable of holding a corresponding plurality of containers.

In an embodiment, means for positioning the container is provided on the tray in a pre-determined orientation.

In an embodiment, means for punching holes through the container is provided wherein the means for punching holes has an interior capable of receiving the light source to emit the beam of light therefrom.

In an embodiment, an auxiliary sensor is provided capable of sensing light outside of the beam of light and originating from the light source.

In an embodiment, a diverter is constructed and arranged in the beam of light. The diverter may be constructed from a transparent material.

In another embodiment of the present invention, a method is provided for sensing status of a container having an interior holding a product requiring the product to be subjected to a process performed by a system. The method comprises the steps of: providing a tray on which the container is placed; inserting the tray into the system such that the container is arranged to perform the process on the product in the interior of the container; and detecting the status of the container in the system.

In an embodiment, the detecting step is performed optically.

In an embodiment, the method further comprises the step of punching a hole in the container after beginning the process.

In an embodiment, the method further comprises the step of punching a hole in the container to indicate a change in the status of the product in the container.

In an embodiment, the method further comprises the steps of: providing a polarizer rotating on an axis; and monitoring changes in polarity in the system wherein a change is indicative of a change in the status of the system.

In an embodiment, the method further comprises the step of providing a polarizer attached to the container.

In another embodiment of the present invention, a system is provided for monitoring status of a container. The system has a polarizing piece attached to the container. A light source is constructed and arranged to form a beam of light in a path wherein the polarizing piece is in the path, and a sensor is in the path of the light wherein the polarizing piece is between the light source and the sensor.

In an embodiment, the system has a rotating polarizer in the path of the beam of light intermediate the sensor and the polarizing piece.

In an embodiment, the system has means for forming an aperture in the container through the polarizing piece.

In an embodiment, the system has means for sensing light originating from a light source outside of the path of the beam of light.

In an embodiment, a diverter is provided in the path of the beam of light.

It is, therefore, an advantage of the present invention to provide a system and a method for detecting status of a container subjected to a process.

Another advantage of the present invention is to provide a system and a method for detecting a change in status of the bag subjected to a process.

Yet another advantage of the present invention is to provide a system and a method for optically detecting a change in status of a bag subjected to a process.

Moreover, an advantage of the present invention is to provide a system and a method for preventing tampering with the product prior to completion or following disruption of the process.

A still further advantage of the present invention is to provide a system and a method that is capable of detecting tampering without affecting completion of the process or capable of providing suitable warning indicative of tampering.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a system and a method for marking containers or other fluid-carrying bags carrying a fluid or mixture within an interior of the container requiring that the fluid or mixture is subjected to a treatment, such as, for example, illumination by ultraviolet (UV) radiation. Also provided is a system and a method for detecting status of a container or bag requiring that the contents of the bag be subjected to a process, such as illumination by UV radiation.

Figure 1:
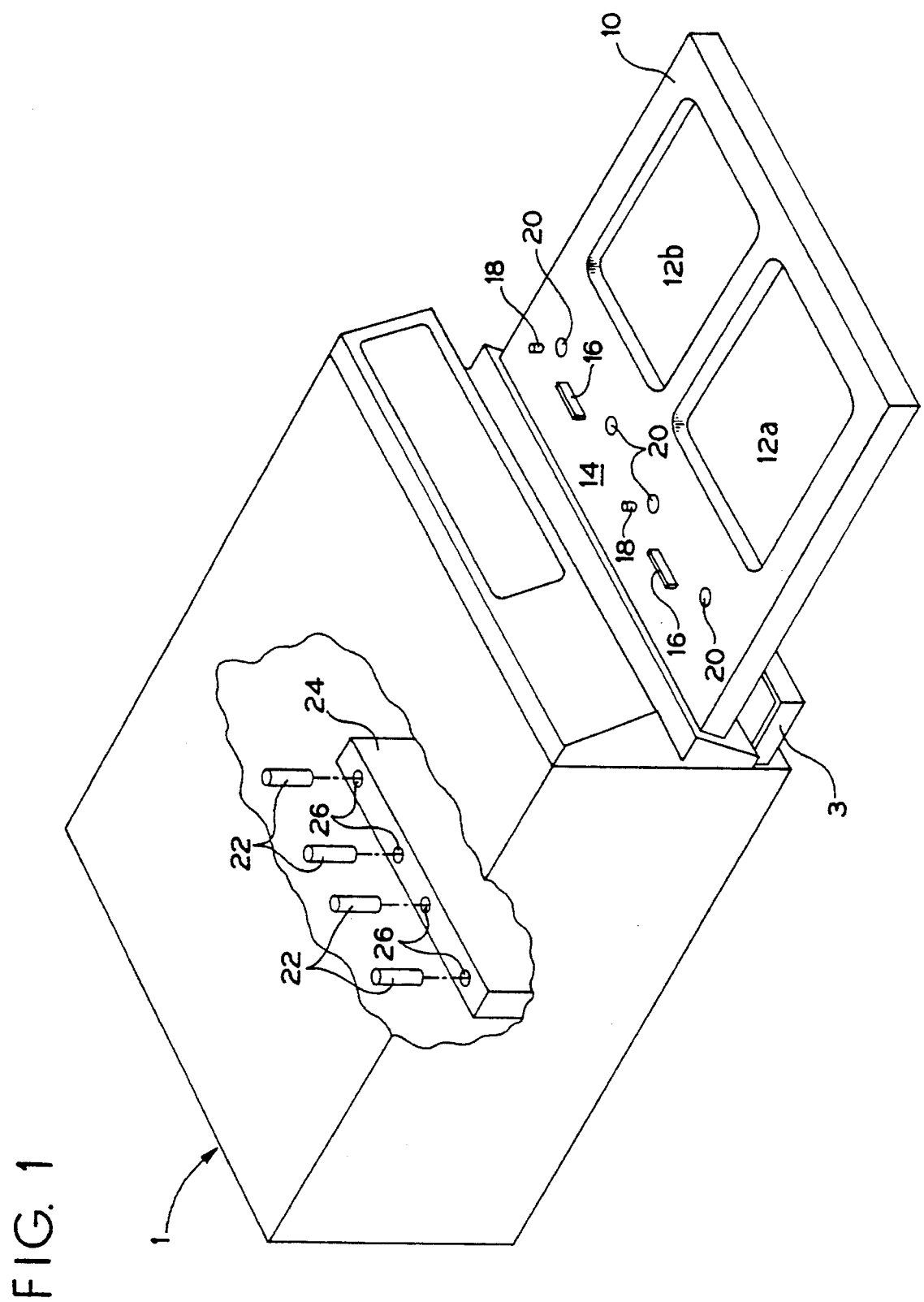
FIG. 1 illustrates a perspective view of a device for holding and punching a container having a product therein requiring that the product be subjected to a process.

Referring now to the drawings, FIG. 1 generally illustrates an illumination system 1. The system 1 is a machine in a housing that is capable of supplying a precise dose of intense red light energy to a disposable plastic bag containing a mixture requiring processing by illumination of the mixture with the intense red light energy. A typical mixture is a blood component, such as human plasma, and methylene blue. The red light activates the methylene blue to release singlet oxygen which inactivates certain viruses in the plasma.

The system 1 has numerous sub-systems required for the illumination and viral inactivation to occur in a safe and efficacious manner. The sub-systems will be briefly described hereinafter. The sub-systems are only related to the present invention in that the sub-systems cooperate with the components of the present invention within the system 1. Therefore, the sub-systems required for viral inactivation are merely provided for background of the overall system.

A first sub-system is a user interface having a power on/off switch, a start action switch and an emergency switch. A beeper and back-lit easy-to-understand icons are further provided and may be custom designed. Icons may be used to designate that the power is "on" for example, if a drawer 10 is ready for use, but is open and should be closed; or a warning that the user is not to open the drawer 10 or else the system 1 may go into a hazard state with a consequent loss of the bag being processed. Other icons may relate to an open drawer indication informing a user that the process is complete, that the drawer 10 is open, or that the bags may be removed. A hazard indication may further be provided informing the user that a procedural error or an internal malfunction has been detected. In either case, the bag present in the system 1 must be removed and discarded following indication of a hazard situation.

In a preferred embodiment, an eleven segment green bar graph signifies the extent of the illumination process occurring in the system 1. A beeper provides audible information that the illumination process has been completed. A display 2 may be provided on the face of the system 1 to provide the data or other visual information to a user.

Control logic provides another sub-system of the present invention wherein the amount of light energy provided during each illumination cycle is monitored continuously by intensity sensors. The information is provided to a programmable gate array which determines the amount of time necessary to provide the desired light energy. The logic also ensures that the machine performs a self-test at power up and continually monitors various temperatures and responds appropriately to various inputs by a user. The control sub-system is capable of running on its own power supply at five volts.

Red light emitting diode (LED) arrays are provided in the system. The drawer 10 is capable of holding two disposable containers simultaneously for viral inactivation within the system 1. Each container is exposed to light from both the top and the bottom so that a total of four arrays in the machine are required. A typical array is approximately fourteen centimeters wide and twenty-three centimeters long and is designed to cover the entire illuminated area of the container.

Each array further typically contains 930 LED's that yield light peaking at approximately 640 to 680 nanometers. The LED's are packed in rows slightly offset so as to maximize density. The LED's may be further mounted a few millimeters off a board so that maximum heat dissipation can be achieved through their leads. The lower arrays of LED's in the system 1 may be combined to form a single monolith for ease of manufacture. Similarly, both upper arrays of LED's may be combined. Each upper and lower monolith may be attached to its own driver board housing the LED driver circuitry (current control), calibration circuitry, primary cooling circuit temperature sensors and red light intensity sensors. The red light intensity sensors measure light passing through the board so as not to be affected by presence or absence of a disposable bag.

A cooling sub-system is also required for cooling the LED arrays. The sub-system consists of two sealed chambers (an upper chamber and a lower chamber) surrounding the LED array board connected by tubing to a pump, a filling port/ bubble trap and a heat exchanger coil. The surface faces the disposable bag and is fitted with a hermetically sealed one-eighth inch thick tempered glass window. The LED arrays are immersed in the heat transfer oil that flows around them and removes heat from their leads. The oil is pumped by a small centrifugal pump through a concentric tube counterflow and heat exchanger coil where the heat is transferred to a refrigerant. Temperature sensors on the LED board enable the control logic to determine whether the LED's are operating at the correct temperature.

A secondary LED array cooling sub-system having a hermetically sealed compressor, evaporator, condenser and expansion valve are provided in a self-contained sub-assembly. The secondary cooling sub-system preferably runs continuously whenever power is turned on. An illumination chamber cooling sub-system is further required having a further centrifugal fan that operates off line voltage. A fan is located behind a series of baffles on a front of the system 1. Air is sucked through a slit below a touch panel and is blown over the disposable bag drawer 10 and across an air temperature sensor then over a refrigerator compressor and out through a port in the back of the system 1. The air temperature sensor provides a reference temperature. If the temperature rises above some empirically determined value, it may be possible that either the fan is not functioning or the bag is being overheated. In either case, the system 1 goes into a hazard state.

A further sub-system consists of a disposable bag shaker. The sub-system has a shaded pole motor that operates on line voltage, a cam and a linkage. A pivoting frame housing the bag marking system of the present invention described hereinafter is provided and is attached to the drawer 10.

A spill tray 3 is further provided as an auxiliary tray below the illumination drawer 10 that is intended to catch any fluid that may accidentally spill from the drawer 10. The spill tray 3 also houses a separate compartment at the back into which fall the slugs punched out by the bag marking system of the present invention to be described hereinafter. A user is directed to empty the slugs out periodically. The spill tray 3 is removable and may be cleaned and disinfected if desired.

The bag marking sub-system of the present invention of the system 1 will now be described with reference to the figures. Referring to FIG. 1, the system 1 includes a drawer 10 on which containers or bag may be placed in bag holding areas 12a, 12b. The bag holding areas 12a, 12b are apertures through the drawer 10 such that a bottom side of the bag in the bag holding areas 12a, 12b may be illuminated by an LED array located beneath the drawer 10.

The drawer 10 slides on drawer slides (not shown) so that the drawer 10 slides entirely out of the system 1. The drawer 10 has locating features at a rear section 14 such that a bag placed in the bag holding area 12a, 12b has its flap extending into the rear section 14. The locating feature in the rear section 14 ensures that the bag cannot be installed incorrectly. To this end, in a preferred embodiment, the bag or container used with the present invention is disclosed and described in co-pending, commonly assigned U.S. patent application Ser. No. 08/359,494, filed concurrently herewith, the disclosure of which is fully incorporated herein by reference. The bag 100 or container has a slit 102 provided in its flap section 104. The slit 102 may be placed over a slit locator 16 such that the flap section 104 of the bag 100 may only be placed on the tray 10 with the slit 102 in the flap section 104 placeable over the slit locator 16.

However, since the slit locator 16 is typically centrally located, the bag 100 may be placed on the drawer 10 such that its top side or its bottom side is facing up. Therefore, an orientating aperture 106 is provided in the bag 100, and an orientating locator 18 is provided on the drawer 10 such that the bag 100 can only be placed on the drawer 10 with its top side facing up and its bottom side facing down through the bag holding areas 12a and 12b.

The orientating locators 18, in an embodiment, are in the shape of a small cylindrical peg. It should be understood, however, that any shape or size may be implemented by those skilled in the art. Likewise, the slit locator 16 may also be variously sized as appropriate to receive the container 10 having a correspondingly sized aperture or slit 102. In a preferred embodiment of the system, the punches 10 are ten millimeter diameter round punches with a pair of punches 22 provided for punching each bag within the system 1.

Also provided in the drawer 10 are punch apertures 20. The punch apertures 20 are constructed and arranged such that punches 22 of the system 1 to be described hereinafter may punch through the punch apertures 20 into a die 24 at the corresponding die apertures 26.

As illustrated and described, the drawer 10 has two bag holding areas 12a and 12b such that the two bags may be processed simultaneously. A single bag may also be processed within the two bag system. It should be understood, however, that the system 10 may be implemented with a drawer capable of holding a single bag or a plurality of bags greater than two.

Figure 2:
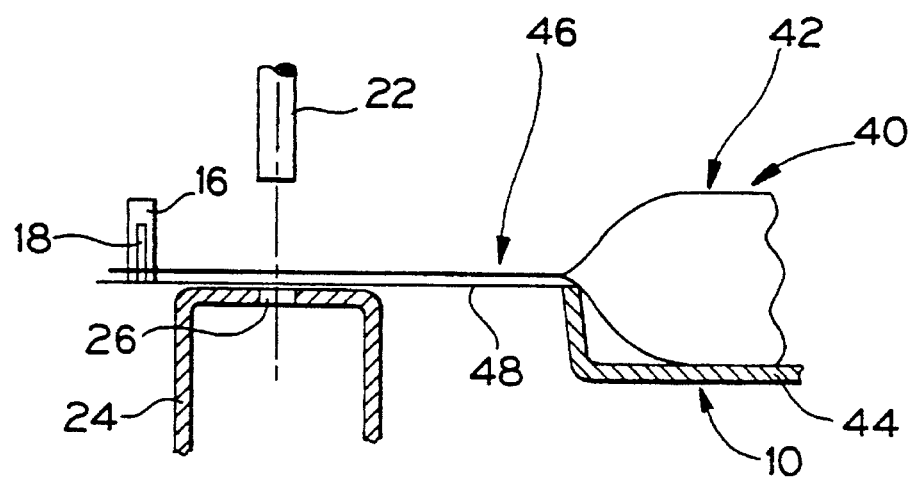
FIG. 2 illustrates a cross-sectional view of a portion of the device illustrated in FIG. 1.
Figure 3:
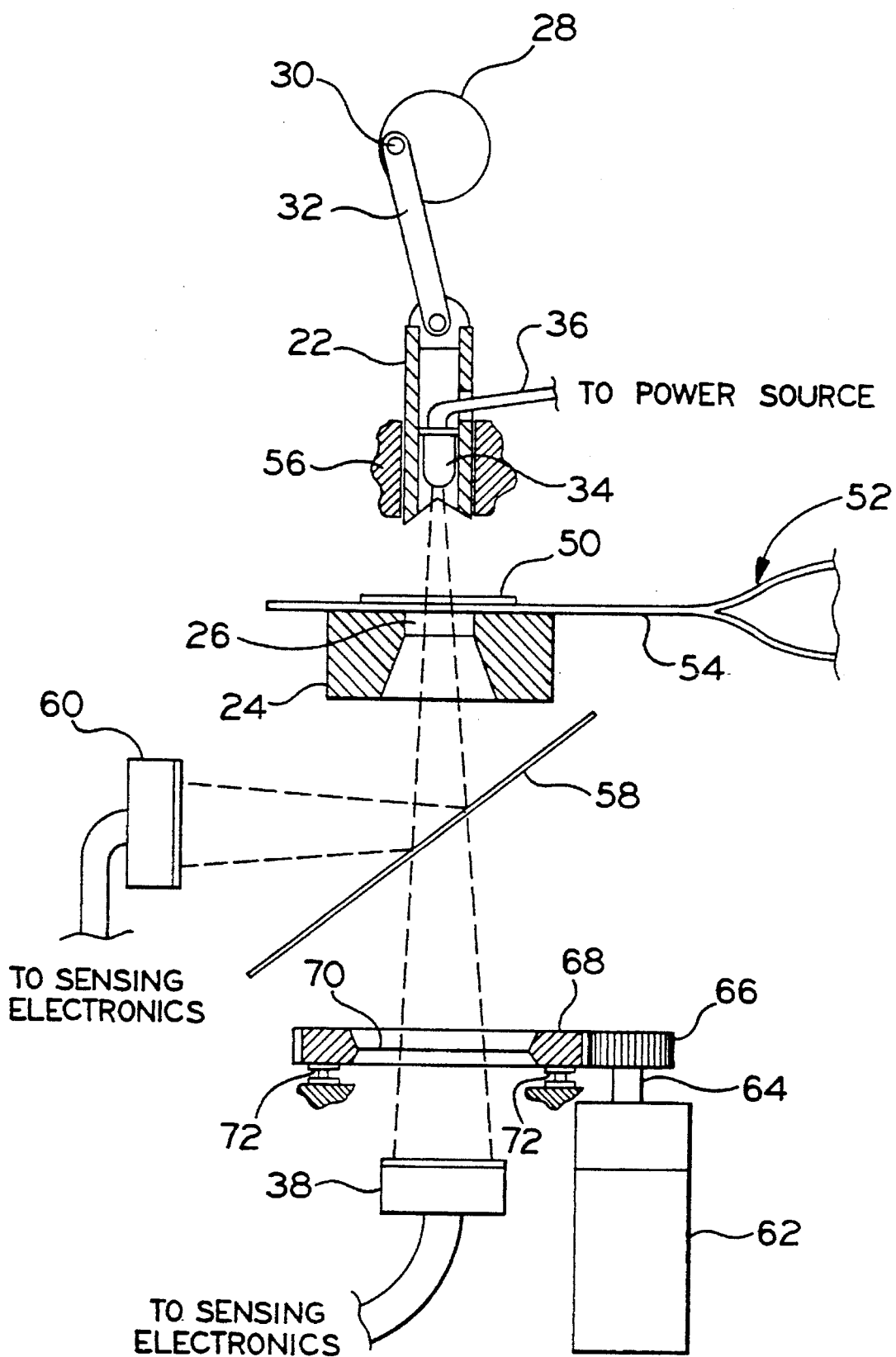
FIG. 3 illustrates a cross-sectional view of additional components of the device illustrated in FIG. 1.
Figure 8:
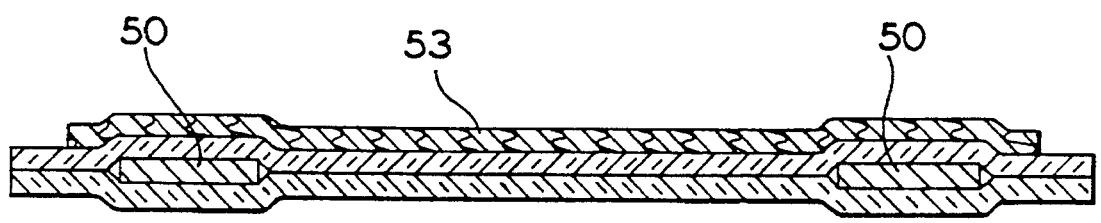
FIG. 8 illustrates a cross-sectional view taken generally along the line V—V of FIG. 5.

Referring now to FIGS. 2 and 3, each of the punches 22 is driven by a motor (not shown) driving a cam 28 mounted on a cam shaft 30. The cam shaft 30 is eccentrically mounted and connected to a connecting rod 32 to the punch 22 by appropriate and suitable attaching means. The cam shaft 30 is driven by a DC gear motor (not shown) with a steel chain drive in a preferred embodiment. The cam shaft 30 has a sensor switch (not shown) that ensures that the cam shaft 30 always returns to a home position. If the cam shaft 30 does not return to its home position, the information is recognized by the control logic of the system 1. The system 1 is in a "hazard state", and an appropriate indication of the same is generated.

The punches 22 are designed to independently punch a hole at the start of an illumination process of the system 1. A second hole is punched by another of the punches 22 at the completion of the illumination process. Therefore, each of the punches 22 is independently controlled for punching the holes in the container placed on the drawer 10 of the system 1.

In another embodiment of the system 1 of the present invention, the punch 22 is hollow as illustrated in FIG. 3 such that a light source 34 connected to appropriate circuitry 36 providing power to the light source 34 is provided. The light source 34 emits light sensed by an optical sensor 38 capable of detecting presence or absence of a hole in the bag. If a hole is formed in the bag, an indication is provided that the punch has punched a hole through the bag, and the illumination process has started. If a second hole is detected by an optical sensor 38 for the same container, the completion of the process may be indicated. If the process is aborted prior to completion, the "finish" holes are not punched and the operator can visually recognize that such bags are "defective" as the illumination process was not completed.

In addition, when a user initiates an illumination process, a sensor 38 corresponds to the punch 22 which punches the bag when the process is started. The sensor 28 can check whether the hole is already punched. If it is punched, the system 1 determines that the bag in the system 1 has already been illuminated or processed. Instead of permitting a second dose of illumination, the system 1 provides a hazard indication to effect removal of the bag. The operator may then remove the bag and visually observe whether the bag has one or two indicator holes punched therethrough. If only one hole is punched, the bag must be discarded as one hole provides an indication that the operation was started but aborted prior to completion. If both the start and finish holes are punched, evidence exists that potentially an attempt was made to give the bag or bags a second dose of illumination.

FIG. 2 generally illustrates a bag 40 positioned on the drawer 10 such that a lumen 42 of the bag 40 is placed on a main body portion 44 of the drawer 10. A bag flap 46 through which punches are made is placed on a flap holding portion 48 of the tray 10. The bag flap 46 has at least two apertures in a preferred embodiment, one aperture secures the bag flap over the slit locator 16, and the other aperture fits over the orientating locator 18 extending substantially perpendicularly from its surface of the flap holding section 48.

The drawer 10 is shown in FIG. 2 in its closed position following placement of the bag 40 on the drawer 10 and properly orientated within the flap 46 and its apertures secured on the slit locator 16 and the orientating locator 18.

Figure 4:
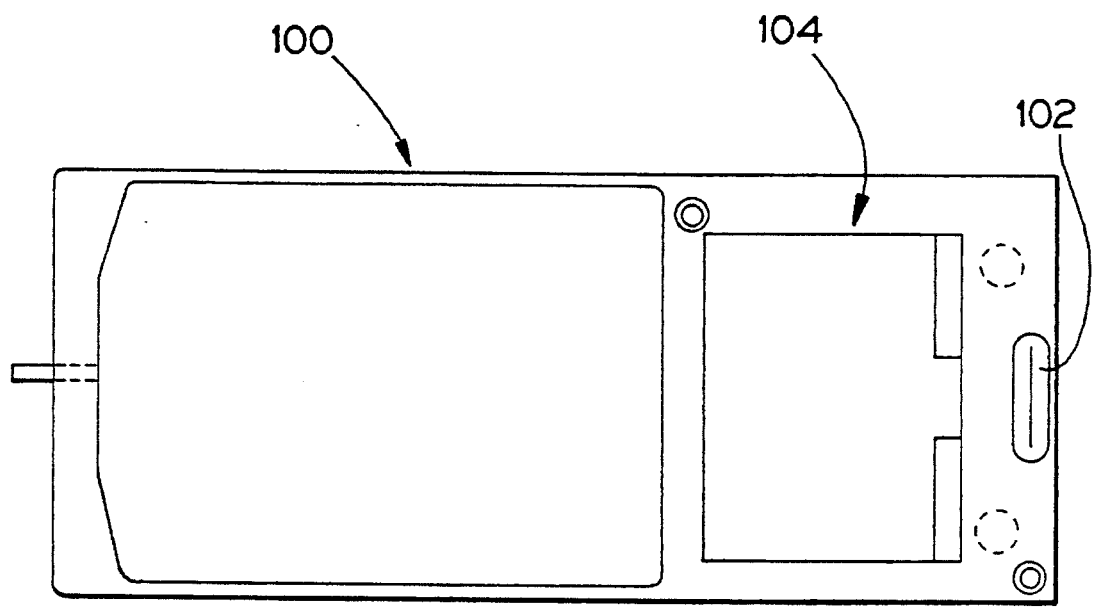
FIG. 4 illustrates a plan view of an embodiment of a fluid-carrying bag or container having a first embodiment of identifiers on the container pursuant to the present invention.
Figure 5:
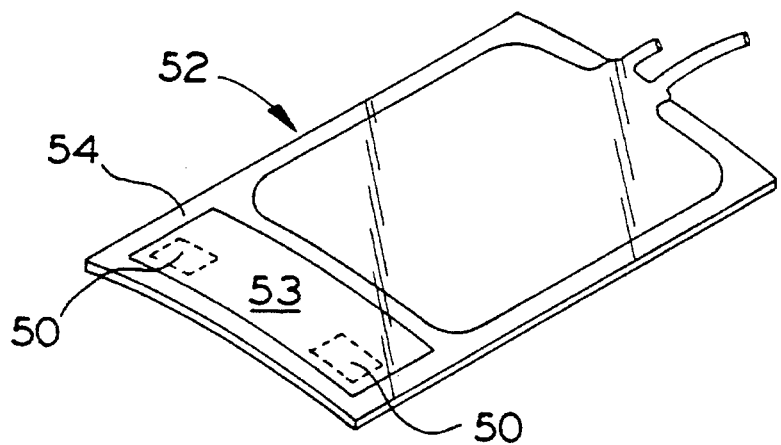
FIG. 5 illustrates a perspective view of another embodiment of a fluid-carrying bag or container with a second embodiment of identifiers on the container pursuant to the present invention.
Figure 6:
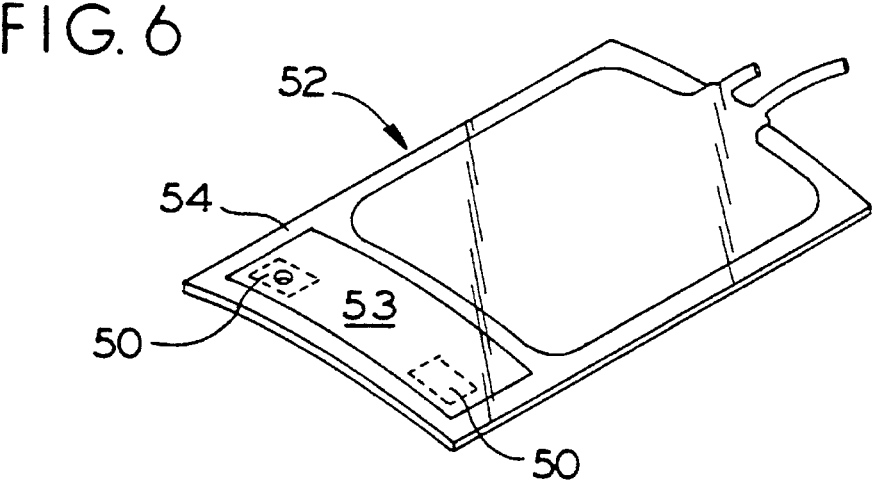
FIG. 6 illustrates a perspective view of an embodiment of the fluid-carrying bag or container of the present invention as illustrated in FIG. 5 following a first step of a process for identifying treatment of contents of the bag or container.
Figure 7:
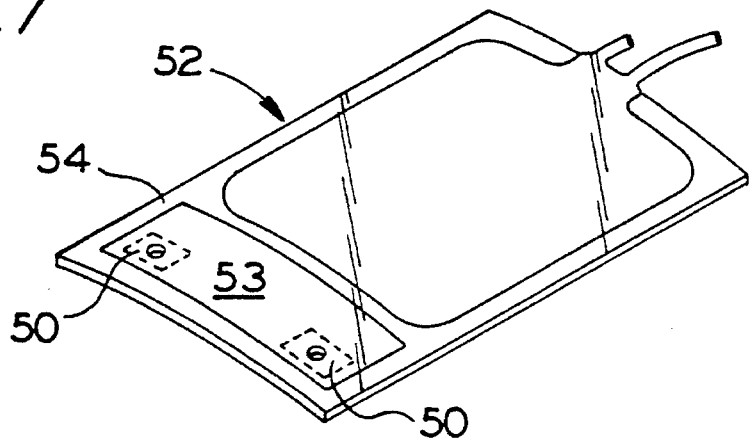
FIG. 7 illustrates a perspective view of a fluid-carrying bag or container of the present invention as illustrated in FIGS. 5 and 6 following a second step of the process for identifying treatment of contents of the bag or container.

In this position, the punch 22 is capable of punching a hole through the bag flap 46 due to the position of the punch aperture 20 in the flap holding portion 48 of the drawer 10 and further in view of placement of the die 24 and its respective die aperture 26. This particular arrangement of the die and punch is particularly suitable for the bag illustrated in FIG. 4 and described in co-pending, commonly assigned U.S. patent application Ser. No. 08/359,494, and illustrated therein.

Referring again to FIG. 3, the additional circuitry and sensors are particularly adaptable for embodiment of the bag illustrated in FIGS. 5–8 and described in co-pending, commonly assigned U.S. patent application Ser. No. 08/359,494. As illustrated in FIGS. 5–8, the locator apertures are not shown. However, the hanging slit aperture and the orientating aperture may be provided as in the embodiment illustrated in FIG. 4.

Using a bag 52 illustrated in FIGS. 3 and 5–8, polarized pieces are incorporated into the bag 52 as generally illustrated at 50 in FIGS. 3 and 5–8. The polarizing piece 50 in the bag 52 as illustrated in FIG. 3 is outside of the seal in a flap region 54 of the bag 52.

As shown and previously described, the flap region 54 is placed immediately above the die 24 such that the die aperture 26 aligns with the punch 22. A punch guide 56 may be provided to maintain vertical alignment and displacement of the punch 22 through the punch aperture 26 of the die 24. A diverter 58 is provided to divert the punched pieces or "slugs" from the flap region 54 and the polarizing piece 50 into the tray 3 for subsequent disposal of the slugs. The diverter 58 is, in a preferred embodiment, a transparent plate such that light from the light source 34 is capable of emitting through the diverter 58 to the sensor 38. An auxiliary optical sensor 60 may be provided to detect any "clogging" on the diverter 58 of the slug or any other matter obstructing light to emit from the light source 34 to the sensor 38.

Further provided in the system 1 is a gear motor 62 having a shaft 64 extending therefrom driving a pinion 66. The pinion 66 drives a ring 68 having gear teeth mating with the pinion 66 so as to rotate the ring 68. The ring 68 includes a polarizing material 70 embedded therein. Ball bearings 72 are provided for support and assistance in rotation of the ring 70. The gear motor 62 may be suitably controlled to rotate the ring 68 at desired speeds. Therefore, the light source 34 and the sensor 38 upon which the light source 34 emits light is provided with a space therebetween into which the bag 52 with the polarizing material 50 is introduced. A second piece of polarizing material 70 in the light path may be included and mounted on the ring 68 to rotate about an axis that passes through the light source 34 and the sensor 38. The polarizing material 70 conditions light incident upon it.

In an embodiment of the present invention, a label 53 may be placed over the polarizing material 50 in the flap region 54 of the bag 52 to conceal the same. The polarizing material may be situated between the flap region 54 and the label 53 or between layers of the flap region 54. The label 53 may include indications or pointers signifying to a user the location of the punched areas in the flap region 54 and what those punches signify.

The light source 34 implemented in the system 1 may be a high intensity light emitting diode. The transparent diverter 58 may be provided to divert the punched out slug to roll or slide away from the path of light from the light source 34 so as not to obstruct the light to the sensor 38.

When a bag 52 or a plurality of bags is placed in the system 1, no hole is yet punched. The sensor 38 senses the light from the light source 34 through the rotating polarizer 70 and sees a signal whose intensity varies sinusoidally as the polarizing material 70 rotates. Therefore, when the polarizing axes of the polarizing material 50 in the flap region 54 of the bag 52 and the second polarizing piece 70 in the ring 68 are at zero degrees with respect to each other, the intensity of the transmitted light is given by the equation:

$$I_s = I_o * T_d * T_h \cos \theta$$

wherein $I_o$ is unhindered intensity of the light source 34, $T_d$ is transmissivity of the polarizing material 50 in the flap region 52 and $T_h$ is transmissivity of the polarizing material 70 in the ring 68. The transmissivity of the polarizing materials are each approximately 0.9.

Under the condition wherein the polarizing axes are at zero degrees with respect to each other, the intensity seen by the sensor 38 is approximately $0.81 I_o$. However, when the axes of the rotating polarizing material 70 in the ring 68 is 90° with respect to the axes of the polarizing material 50 in the flap region 54, the intensity seen by the sensor 38 is zero by the above equation (cosine 90°=0). Therefore, a measurable variation in the intensity sensed by the sensor 38 permits the process to proceed with appropriate controls responsive to the sensed conditions.

When the process of illumination of the bag 52 begins, the punch 22 is driven towards the die 24 by a mechanism such as a motor or fluid cylinder, and a hole is punched in the flap region 54 of the bag 52 through the polarizing material 50. Similarly, when the process is completed, a second punch 22 punches a hole through the bag at the other location for the punched hole as shown in FIGS. 4–7. The system 1 then prompts the operator to remove the bag 52 from the drawer 10. If the operator does not do so, but tries to restart the process, the sensor 38 sees a continuous high intensity signal since holes are now punched in the flap region 54 and concludes that the bag 52 has already been processed and suitably warns the operator. If the operator, on the other hand, tries to defeat the system by putting, for example, a piece of tape over a hole, the sensor 38 sees a constant signal at some lower level (less than $I_s$) and, therefore, concludes that a malfunction in the system 1 exists and the operator can be suitably warned.

Figure 9:
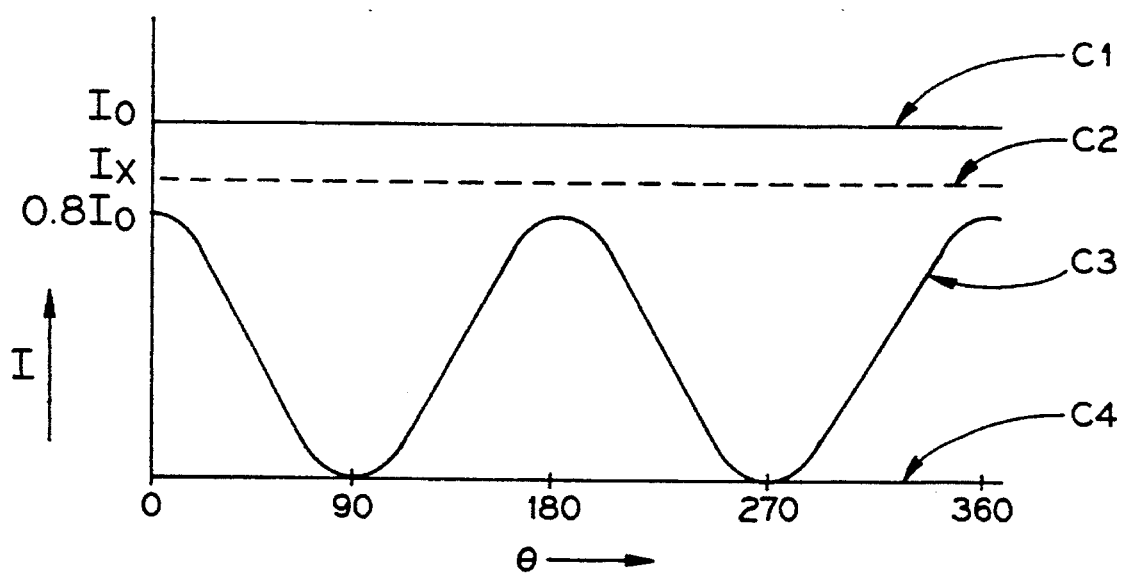
FIG. 9 illustrates a graph of intensities over phase as detected by an embodiment of the system of the present invention.

FIG. 9 illustrates responses from the sensor 38 in the system 1 under various conditions by plotting intensity versus phase. When a hole is present or no bag is present in the system, the constant intensity designated at C1 is sensed by the sensor 38. If a translucent material is placed in the hole, such as a piece of tape, or the like, or a user is attempting to defeat the system, an intensity less than the intensity $I_o$ and designated $I_s$ and further designated by the line C2 would be sensed. A condition wherein the bag has not been punched results in a sinusoidal signal as indicated by the sign C3. If an opaque material is placed over the hole, such as a piece of electrical tape from a user attempting, for example, to defeat the system 1, zero intensity would be sensed as indicated by C4.

The auxiliary sensor 60 may be implemented for convenience where its output will always be constant therefore functioning as a base line such that the difference between outputs of the sensors 38 and 60 will be constant in all cases except when a new bag without a punched hole is placed in the system 1.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A system for detecting status of a container having an interior holding a product requiring the product to be subjected to a process, the system comprising:

a housing defining an interior;

a tray on which the container is placed wherein the tray is insertable into the interior of the housing;

a light source positioned to transmit a beam of light through the container in the housing; and a sensor constructed and arranged to detect the beam of light and its intensity; and means for punching holes through the container wherein the means for punching holes has an interior capable of receiving the light source to emit the beam of light therefrom.

2. The system of claim 1 further comprising:

a rotating polarizer constructed and arranged to rotate in the beam of light.

3. The system of claim 1 further comprising:

a static polarizer attached to the container wherein the static polarizer is capable of having a punch made therethrough.

4. The system of claim 1 further comprising:

a plurality of receiving sections in the tray capable of holding a corresponding plurality of containers.

5. The system of claim 1 further comprising:

means for positioning the container on the tray in a predetermined orientation.

6. The system of claim 1 further comprising:

an auxiliary sensor capable of sensing light outside of the beam of light and originating from the light source.

7. The system of claim 1 further comprising:

a diverter constructed and arranged in the beam of light.

8. The system of claim 7 wherein the diverter is constructed from a transparent material.

9. A method for sensing status of a container having an interior holding a product requiring the product to be subjected to a process performed by a system, the method comprising the steps of:

providing a housing defining an interior;

providing a tray on which the container is placed;

inserting the tray into the interior of the housing such that the container is arranged to perform the process on the product in the interior of the container;

detecting the status of the container in the housing; and punching a hole in the container after beginning the process.

10. The method of claim 9 wherein the detecting step is performed optically.

11. The method of claim 9 further comprising the steps of:

providing a polarizer rotating on an axis; and monitoring changes in polarity in the system wherein a change is indicative of a change in the status of the system.

12. The method of claim 9 further comprising the step of:

providing a polarizer attached to the container.

13. A system for monitoring status of a container, the system comprising:

a polarizing piece attached to the container;

a light source constructed and arranged to form a beam of light in a path wherein the polarizing piece is in the path;

a sensor in the path of the light wherein the polarizing piece is between the light source and the sensor; and means for forming an aperture in the container through the polarizing piece.

14. The system of claim 13 further comprising:

a rotating polarizer in the path of the beam of light intermediate the sensor and the polarizing piece.

15. The system of claim 13 further comprising:

means for sensing light originating from the light source outside of the path of the beam of light.

16. The system of claim 13 further comprising:

a diverter in the path of the beam of light.

17. A system for detecting status of a container having an interior holding a product requiring the product to be subjected to a process, the system comprising:

a tray on which the container is placed;

a light source positioned to transmit a beam of light through the container;

a sensor constructed and arranged to detect the beam of light and its intensity; and means for punching holes through the container wherein the means for punching holes has an interior capable of receiving the light source to emit the beam of light therefrom.

18. A method for sensing status of a container having an interior holding a product requiring the product to be subjected to a process performed by a system, the method comprising the steps of:

providing a tray on which the container is placed;

inserting the tray into the system such that the container is arranged to perform the process on the product in the interior of the container;

detecting the status of the container in the system; and punching a hole in the container after beginning the process.

19. A method for sensing status of a container having an interior holding a product requiring the product to be subjected to a process performed by a system, the method comprising the steps of:

providing a tray on which the container is placed;

inserting the tray into the system such that the container is arranged to perform the process on the product in the interior of the container;

detecting the status of the container in the system; and punching a hole in the container to indicate a change in the status of the product in the container.

20. A method for sensing status of a container having an interior holding a product requiring the product to be subjected to a process performed by a system, the method comprising the steps of:

providing a housing defining an interior;

providing a tray on which the container is placed;

inserting the tray into the interior of the housing such that the container is arranged to perform the process on the product in the interior of the container; and punching a hole in the container to indicate a change in the status of the product in the container.

21. The method of claim 20 further comprising the step of:

detecting the status of the container in the housing.

22. The method of claim 20 further comprising the steps of:

providing a polarizer rotating on an axis; and monitoring changes in polarity in the system wherein a change is indicative of a change in the status of the system.

23. The method of claim 22 further comprising the step of:

providing a polarizer attached to the container.

\* \* \* \* \*